US006432314B1

(12) United States Patent
Storch et al.

(10) Patent No.: US 6,432,314 B1
(45) Date of Patent: Aug. 13, 2002

(54) ANION EXCHANGE MATERIALS AND PROCESSES

(75) Inventors: Joachim Storch, London; Robert Neil Hanley; Richard Neil Templar Freeman, both of Surrey, all of (GB)

(73) Assignee: Biocompatibles Limited, Surrey (GB)

( * ) Notice: Subject to any disclaimer, the term of this patent is extended or adjusted under 35 U.S.C. 154(b) by 0 days.

(21) Appl. No.: 09/308,496

(22) PCT Filed: Nov. 20, 1997

(86) PCT No.: PCT/GB97/03192

§ 371 (c)(1),
(2), (4) Date: Jul. 26, 1999

(87) PCT Pub. No.: WO98/22517

PCT Pub. Date: May 28, 1998

(30) Foreign Application Priority Data

Nov. 20, 1996 (GB) ............................................. 9624130

(51) Int. Cl.$^7$ .................................................. C02F 1/42
(52) U.S. Cl. ........................ 210/679; 210/683; 521/28; 521/31; 521/32; 521/33
(58) Field of Search ................................ 210/638, 679, 210/683, 686; 502/401, 402; 521/27, 28, 31, 32, 33

(56) References Cited

U.S. PATENT DOCUMENTS

| | | | | |
|---|---|---|---|---|
| 3,839,237 A | * | 10/1974 | Battaerd et al. ............ | 210/686 |
| 4,517,241 A | * | 5/1985 | Alpert ........................ | 502/401 |
| 4,797,187 A | * | 1/1989 | Davis et al. .................. | 521/32 |

FOREIGN PATENT DOCUMENTS

| | | | | |
|---|---|---|---|---|
| JP | 7-184989 | 7/1995 | ........... | A61L/33/00 |
| WO | 93/01221 | 1/1993 | ......... | C08F/246/00 |
| WO | 93/14127 | 7/1993 | ........... | C07K/17/02 |

OTHER PUBLICATIONS

Chemistry and Physics of Lipids, vol. 74, 1994, pp. 141–150, "Divalent Cation–dependent Interaction of Sulfated Polysaccharides with Phosphatidylcholine and Mixed Phosphatidylcholine/Phosphatidylglycerol Liposomes", Steffan, Gerhard et al.

J. Chromatog.Sci, vol. 27, No. 4, 1989, pp. 176–185, "Zwitterionic Stationary Phases in HPLC", Yu, Louis W. et al.

International Symp. Chromatog., 35th Anniv. Res. Group Liq. Chrom. JPN., 1995, pp. 593–597, "Multifunctional Ion–exchange Stationary Phases for HPLC", Yang, Mei–Hui et al.

J. Chromatogr., A, vol. 722(1+2), 1996, pp. 87–96, "Multifunctional Ion–exchange Stationary Phases for High–performance Liquid Chromatography", Yang, Mei–Hui et al.

J. Biomater. Sci. Polymer EDN., vol. 6, No. 8, 1994, pp. 707–714, "Interaction of Heparin with Amphiphile Assemblies and Biocompatibility of the Heparin Complexes", ITO, Yoshihiro et al.

* cited by examiner

*Primary Examiner*—Ivars Cintins
(74) *Attorney, Agent, or Firm*—Sughrue Mion, PLLC

(57) ABSTRACT

Anion exchange material surfaces are provided with zwitterionic and cationic groups, preferably by coating with a polymer formed from monomers including a zwitterionic monomer, a cationic monomer and, optionally, a termonomer providing stable binding at the substrate surface. The ion exchange materials may be used to scavenge heparin from blood by an ion exchange separation process. The zwitterionic group reduces the rate of fouling by biological materials such as proteins.

31 Claims, No Drawings

ANION EXCHANGE MATERIALS AND PROCESSES

The present invention relates to anion exchange separation processes and novel polymers for use in such processes. It relates especially to processes in which anionic components such as anticoagulants are removed from blood.

In WO-A-93/01221 we describe various polymers and their use to coat surfaces to improve their biocompatibility. The polymers include zwitterionic groups and pendant groups which are capable of providing stable surface binding of the polymer to underlying substrate surfaces. The binding may be by provision of pendant hydrophobic groups which physisorb onto hydrophobic substrates, by counterionic attraction between pendant ionic groups on the polymer and oppositely charged groups at the substrate surface, by providing covalent attachment between coreactive pendant groups on the polymer and groups at the substrate surface or by crosslinking the polymer after coating. Post coating crosslinking may also be used to improve the stability of a polymer which is physisorbed, covalently bonded or counterionically bonded to the surface. The polymers have good hemocompatibility as indicated by the low platelet adhesion values reported in that specification.

It has also been shown that zwitterionic groups at substrate surfaces, for instance of contact lenses, show lower rates of deposition of proteins and lipids from biological liquids such as tear film. In WO-A-92/07885, reduced levels of protein deposition are described for contact lenses formed from a hydrogel of a crosslinked copolymer of copolymerisable zwitterionic monomer and non ionic comonomer.

In WO-A-93/21970 it is disclosed that microorganisms, especially bacteria, adhere to surfaces having pendant phosphoryl choline groups less than to similar surfaces without such groups present.

Another way of reducing the thrombogenicity of surfaces has involved attachment or adsorption of anti-thrombogenic active compounds to substrate surfaces. For instance heparin may be attached through covalent or counterionic bonding to surfaces. In U.S. Pat. No. 3,634,123 the binding of heparin to a surface was increased by incorporation of cationic surfactant. A related process is described in EP-A-0350161, in which a surface is first coated with a cationic surfactant and subsequently with heparin. In EP-A-0086187 the surface is first coated with a cationic polymer and subsequently with heparin. In JP-A-53/137268 a cross-linked acrylic copolymer of a cationic monomer and a polyethyleneglycol monomer is blended with polyurethane and made into tubing which can be coated with heparin. In EP-A-0086186 heparin is attached to an underlying surface through a covalent bond via the end carbohydrate unit. In U.S. Pat. No. 5,342,621, a complex of heparin with phosphatidyl choline and admixed with a polymer of caprolactone or L-lactic acid (both of which have no overall charge) and subsequently used to coat medical devices.

Generally patients who are undergoing complex operations requiring that their blood be directed through extra corporeal circuitry, require administration of heparin into the circulation to prevent the blood clotting. Subsequently the heparin has to be neutralised or removed from the blood stream. In order to remove heparin from the circulation without administering a further active compound to neutralise the heparin, it has been suggested to immobilise protamine, a cationic polypeptide used to neutralise heparin, at the surfaces of a filter used in an extra corporeal blood circuit, to scavenge heparin from a patient who has been systemically heparinised.

In J. Chromatography A (1996) 722, 87–96 and Int. Symp. Chromatog. 35$^{th}$ Anniv. Res. Group Liq. Chrom. Jpn 1995, 593–597, Yang et al describe ion exchange stationary phases for HPLC. The materials were based on silica to which organic groups including secondary amine groups were attached which in turn were partially derivatised to zwitterionic groups.

In a new ion exchange process according to the invention a substrate has at its surface zwitterionic pendant groups and cationic pendant groups having anionic counterions and is contacted with an aqueous solution having suspended or dissolved therein an anionically charged compound, whereby the anionic compound is ion exchanged with the counterions.

The process is of particular value for treatment of blood, especially for scavenging clotting inhibitors, for instance anionic mucopolysaccharides. The anionically charged mucopolysaccharide may be heparin or a similar is anti-thrombogenic compound such as hirudin or chondroitin sulphate, or may be alginate or hyaluronic acid. The provision of zwitterionic groups seems to minimise adsorption of other components from blood or biological fluids contacted with the substrate surface, thereby preventing fouling of the surface which may prevent ion exchange taking place. In the process of the invention the zwitterionic group, hereinafter referred to as a group X, preferably has a permanent cation, that is a quaternary ammonium or phosphonium or a tertiary sulphonium group. The cationic group at the surface, similarly, is preferably permanently cationic and thus not pH sensitive. The cationic group is preferably a group $N^+R^5_3$, $P^+R^5_3$ or $S^+R^5_2$ in which the groups $R^5$ are the same or different and are each $C_{1-4}$-alkyl or aryl (preferably phenyl) or two of the groups $R_5$ together with the heteroatom to which they are attached from a saturated or unsaturated heterocyclic ring containing from 5 to 7 atoms, preferably the cationic group is $N^+R^5_3$ in which each $R^5$ is $C_{1-4}$-alkyl, preferably methyl.

It is preferred for the anion of the zwitterion to be a phosphate or a phosphonate group, usually a phosphate ester and is most preferably a phosphate diester and thus having a single negative charge.

Most preferably X is a group of formula

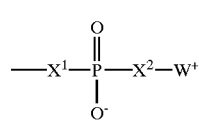

(VI)

in which the moieties $X^1$ and $X^2$, which are the same or different, are —O—, —S—, —NH— or a valence bond, preferably —O—, and $W^+$ is a group comprising an ammonium, phosphonium or sulphonium cationic group and a group linking the anionic and cationic moieties which is preferably a $C_{1-12}$-alkylene group.

Preferably W contains as cationic group an ammonium group, more preferably a quaternary ammonium group.

The group $W^+$ may for example be a group of formula —$W^1$—$N^+R^{23}_3$, —$W^1$—$P^+R^{23a}_3$, —$W^1$—$S^+R^{23a}_2$ or —$W^1$—Het$^+$ in which:

$W^1$ is alkylene of 1 or more, preferably 2–6 carbon atoms optionally containing one or more ethylenically unsaturated double or triple bonds, disubstituted-aryl, alkylene aryl, aryl alkylene, or alkylene aryl alkylene, disubstituted cycloalkyl, alkylene cycloalkyl, cycloalkyl alkylene or alkylene cycloalkyl alkylene, which group $W^1$ optionally contains one or more fluorine substituents and/or one or more functional groups; and either the groups $R^{23}$ are the same or different and each is hydrogen or alkyl of 1 to 4 carbon atoms, preferably methyl, or aryl, such as phenyl or two of the groups $R^{23}$ together with the nitrogen atom to which they are attached form a heterocyclic ring containing from 5 to 7 atoms or the three groups $R^{23}$ together with the nitrogen atom to which they are attached form a fused ring structure containing from 5 to 7 atoms in each ring, and optionally one or more of the groups $R^{23}$ is substituted by a hydrophilic functional group, and the groups $R^{23a}$ are the same or different and each is $R^{23}$ or a group $OR^{23}$, where $R^{23}$ is as defined above; or Het is an aromatic nitrogen-, phosphorus- or sulphur-, preferably nitrogen-, containing ring, for example pyridine.

Preferably $W^1$ is a straight-chain alkylene group, most preferably 1,2-ethylene.

Preferred groups X of the formula VI are groups of formula VA.

The groups of formula (VA) are:

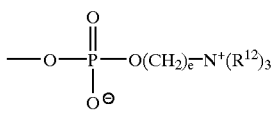

(VA)

where the groups $R^{12}$ are the same or different and each is hydrogen or $C_{1-4}$ alkyl, and e is from 1 to 6, preferably 2 to 4.

Preferably the groups $R^{12}$ are the same. It is also preferable that at least one of the groups $R^{12}$ is methyl, and more preferable that the groups $R^{12}$ are all methyl.

Preferably e is 2 or 3, more preferably 2. When X is a group of formula (VA) preferably B is a group of formula $-(CR^{13}_2)-$ or $-(CR^{13}_2)_2-$, eg. $-(CH_2)-$ or $-(CH_2CH_2)-$.

The cationic group is preferably a group $N^+R^5_3$, $P^+R^5_3$ or $S^+R^5_2$ in which the groups $R^5$ are the same or different and are each $C_{1-4}$-alkyl or aryl (preferably phenyl) or two of the groups $R^5$ together with the heteroatom to which they are attached from a saturated or unsaturated heterocyclic ring containing from 5 to 7 atoms. Preferably $Q^1$ is $N^+R^5_3$ in which each $R^5$ is $C_{1-4}$-alkyl, preferably methyl.

The counterion is a suitable ion, preferably derived from a strong acid, most preferably an acid having a pKa less than 1 for instance less than 0, more preferably less than −1 for instance an inorganic acid. Preferably the counterion is a halide, most preferably chloride.

In the ion exchange process the surface has cationic and zwitterionic groups immobilised at the surface of a substrate which is usually in particulate or membrane form. Membranes may be made of regenerated cellulose in hollow fiber form. Such fibers may be provided with the desired pendant groups by coating with a preformed polymer containing both cationic and zwitterionic groups, which can be crosslinked after coating using crosslinkable monomers as described below. Alternatively cationic and zwitterionic monomers may be graft polymerised directly onto the surface of the cellulose fibers using the process described in U.S. Pat. No. 5,453,467 using suitable monomers, of the general type described below. Alternatively such monomers could be graft polymerised onto soluble cellulose which is subsequently coated onto the fibers using the general technique described in WO-A-93/15775. Terpolymers described below can be used successfully to coat various substrates including polyesters, polycarbonates, polypropylene, polyvinyl chloride and steel and filters may include coated surfaces of any of these materials. Alternatively the polymer could be formed in the presence of a crosslinking monomer having two or more ethylenically unsaturated groups to form a crosslinked material which can be used in bulk as the ion exchange material.

The substrate may be any of those used for ion exchange, for instance based on cross-linked acrylic polymers or polystyrene based polymers or may be based on silica supports. Such substrates with suitable reactive groups, such as amine, carboxylate or hydroxyl groups are available. Alternatively they can be generated; for instance a silica substrate can be reacted with a silane such as a trimethoxy silane having an amine, chlorobenzyl or glycidoxy substituent. Reagents for attaching cationic groups to surface hydroxyl, amine or carboxylate groups are described in our earlier publication WO-A-9106020 while reagents for attaching zwitterionic groups are described in our earlier publications WO-A-9113639 and WO-A-9207858. Crosslinked polymers including zwitterionic monomers can be made as described in WO-A-9207885.

The preferred approach is to coat a particulate or membrane substrate with a preformed polymer having pendant cationic and zwitterionic groups.

The polymer having pendant zwitterionic and cationic groups is generally a copolymer of copolymerisable monomers. Whilst it is most convenient for the polymer to be formed by addition polymerisation of ethylenically unsaturated monomers, it may alternatively be a condensation polymer, or an alternative type of addition polymer, for instance formed by ring opening cyclic monomers.

Copolymers of ethylenically unsaturated monomers may be formed from monomers including a) a zwitterionic monomer of the formula I

YBX    I wherein B is a bond or a straight or branched alkylene, alkylene-oxa-alkylene or alkylene-oligooxa-alkylene group, any of which optionally include one or more fluorine substituents;

X is an organic group having a zwitterionic moiety preferably as described above; and Y is an ethylenically unsaturated polymerisable group; and b) a cationic monomer of the formula II $Y^1B^1Q^1$    II wherein $B^1$ is a bond or a straight or branched alkylene, alkylene-oxa-alkylene or alkylene-oligooxa-alkylene group, any of which optionally includes one or more fluorine substituents;

$Y^1$ is an ethylenically unsaturated polymerisable group; and $Q^1$ is an organic group having a cationic moiety, preferably as described hereinbefore.

Preferably a copolymer includes additional pendant groups capable of providing stable bonding at the substrate surface. Such groups are generally introduced by incorporation of termonomers into the polymerisation. A termonomer may, for instance, include a hydrophobic group which provides for physisorption at the surface, where the substrate surface is hydrophobic, or may comprise a covalent reactive group which is capable of forming a covalent bond with coreactive groups at the substrate surface. Alternatively the copolymer may be crosslinked after coating by subjecting a polymer having pendant crosslinkable groups to conditions such that crosslinking takes place.

A termonomer which has a hydrophobic group is generally of the formula III $$Y^2B^2Q^2 \qquad\qquad III$$

wherein $B^2$ is a bond or a straight or branched alkylene, alkylene-oxa-alkylene or alkylene-oligooxa-alkylene group, any of which may optionally include one or more fluorine substituents;

$Y^2$ is an ethylenically unsaturated polymerisable group; and $Q^2$ is an organic group having a hydrophobic group selected from alkyl groups having at least six carbon atoms, fluorine substituted alkyl groups and alkyl groups having at least one siloxane substituent.

A covalent reactive termonomer may have the general formula IV:

$$Y^3B^3Q^3 \qquad\qquad IV$$

wherein $B^3$ is a bond or a straight or branched alkylene, alkylene-oxa-alkylene or alkylene-oligooxa-alkylene group, any of which optionally includes one or more fluorine substituents;

$Y^3$ is an ethylenically unsaturated polymerisable group; and $Q^3$ is an organic group having a reactive group capable, on imposition of an external stimulus, of reacting with a coreactive group on the surface of a substrate or which is pendant on the polymer.

Reactive groups $Q^3$ may also provide crosslinkability on the polymer. For instance such groups may react with each other or may react with different coreactive groups as pendant groups on the copolymer, for instance amine or, more usually, hydroxyl groups. Examples of reactive groups capable of crosslinking with such pendant groups or of reacting to provide covalent binding to a surface, for example an aldehyde group or a silane or siloxane group containing one or more reactive substituents such as halogen, for example chlorine, or alkoxy, generally containing from 1 to 4 carbon atoms, for example methoxy or ethoxy, or, more preferably, $Q^3$ is a hydroxyl, amino, carboxyl, epoxy, —CHOHCH$_2$Hal, (in which Hal is a halogen atom such as chlorine, bromine or iodine) succinimido, tosylate, triflate, imidazole carbonyl-amino or optionally substituted triazine group.

Preferred reactive comonomers IV which are used to crosslink the comonomer, rather than provide covalent binding to the surface, are those $Q^3$ contains a crosslinkable cinnamyl, epoxy, —CHOHCH$_2$Hal (in which Hal is a halogen atom), methylol, silyl, an ethylenically unsaturated crosslinkable group, such as an acetylenic, diacetylenic, vinylic or divinylic group, or an acetoacetoxy or chloroalkyl sulfone, preferably chloroethyl sulphone, group.

In each of the monomers I to IV the ethylenically unsaturated group is preferably selected from

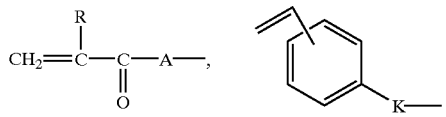

$CH_2=C(R)-CH_2-O-$, $CH_2=C(R)-CH_2OC(O)-$, $CH_2=C(R)OC(O)-$, $CH_2=C(R)O-$, and $CH_2=C(R)CH_2OC(O)N(R^1)-$ wherein:
R is hydrogen or a $C_1-C_4$ alkyl group;

A is —O— or —NR$^1$— where R$^1$ is hydrogen or a $C_1-C_4$ alkyl group or R$^1$ is —B-X, $B^1Q^1$, $B^2Q^2$ or $B3Q^3$ where B, B$^1$, B$^2$, B$^3$, Q$^1$, Q$^2$ and Q$^3$ and X are as defined above in the respective formulae I, II, III and IV and K is a group —(CH$_2$)$_p$OC(O)—, —(CH$_2$)$_p$C(O)O—, —(CH$_2$)$_p$OC(O)—, —(CH$_2$)$_p$NR$^2$—, —(CH$_2$)$_p$NR$^2$C(O)—, —(CH$_2$)$_p$C(O)NR$^2$—, —(CH$_2$)$_p$NR$^2$C(O)O—, —(CH$_2$)$_p$OC(O) NR$^2$—, —(CH$_2$)$_p$NR$^2$C(O)NR$^2$—, (in which the groups R$^2$ are the same or different) —(CH$_2$)$_p$O—, —(CH$_2$)$_p$SO$_3$—, or, optionally in combination with B, a valence bond and p is from 1 to 12 and R$^2$ is hydrogen or a $C_1-C_4$ alkyl group.

Preferably the ethylenically unsaturated groups of all monomers copolymerised together are either the acrylate type or are the styrene type, and, most preferably each has the same formula.

Preferably the zwitterionic monomer has the general formula VI

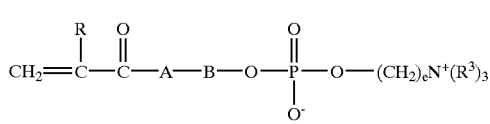

wherein R, A and B are defined above, the groups R$^3$ are the same or different and each is hydrogen $C_{1-1}$ alkyl, aryl, alkaryl, aralkyl, or two or three of the groups R$^1$ with the nitrogen atom to which they are attached form a saturated or unsaturated hetero cyclic ring, and e is 1 to 6, preferably 2 to 4.

Terpolymers formed from the above mentioned zwitterionic monomer, a cationic comonomer of the formula II and a hydrophobic monomer of the formula III as well as some quaterpolymers are novel compounds and are claimed in our copending application filed even date herewith (agents ref HMJ02820WO).

By incorporating pendant groups to provide stable binding on the surface, the terpolymers can be stably bound to many types of underlying surface.

Instead of passing anticoagulant-treated blood through n extra corporeal filter, heparin (or other anticoagulant) scavenging may be carried out by implanting, permanently or temporarily, a device into the body in the circulation, which can remove anticoagulant which has been administered systemically. Thus the zwitterion and cation group carrying surface may be the surface of a vascular stent introduced into a blood vessel of a patient. In this embodiment the device may act as a reservoir, formed in situ, of active ingredient which may be released slowly into the circulation over an extended period of time. Alternatively a device may be preloaded with counterionically charged mucopolysaccharide or other active anionic compound, prior to implantation, to act as a slow release drug delivery system. In this system the anionic mucopolysaccharide or other anionic active compound is the counterion which is anion exchanged in the process of the invention.

The process of the present invention may include a subsequent step of recovering the anionic compound from the substrate by treating it with a second aqueous liquid containing a suitable anion regenerant which anion exchanges to displace the anionic compound.

The proportions of zwitterionic and cationic pendant groups in polymers used in the present processes and products depends upon the desired end use. Where high levels of mucopolysaccharide are to be scavenged from a fluid composition and/or it is desired for a high density of anionic mucopolysaccharide to be deposited onto a surface for subsequent use, then the amount of cationic pendant group should be relatively high as compared to the levels of zwitterionic groups. However where lower levels of mucopolysaccharide are required to be adsorbed to achieve anti-thrombogenic performance, whilst minimising deposition of protein and lipid components and platelets forms an important characteristic of the surfaces, then high levels of zwitterionic pendant groups are likely to be desirable. The relative ratios (equivalents) is in the range 1:100 to 100:1 (zwitterionic to ionic) preferably 1:10 to 10:1, more preferably 1:2 to 20:1.

Termonomer may be present in a monomer mix, for instance to provide the polymer with adsorption properties at a surface or covalent bonding to an underlying substrate, termonomers may be used. The total molar proportion of such termonomer in the polymer may be in the range 0.1 to 75%.

The copolymers and terpolymers may include diluent comonomer. Such diluent comonomer may be used in quantities up to 90 mol %, usually less than 50 mol %. Copolymerisable nonionic monomers may be used such as $C_{1-24}$ alkyl(meth)acrylates, -(meth)acrylamides, and hydroxy $C_{1-24}$ alkyl(meth)acrylates and (meth)acrylamides.

The copolymers or terpolymers may include anionic pendant groups, to provide intermolecular crosslinking by counterionic bonding with cationic groups. In such cases, the equivalent level of anionic groups is lower than that of cationic groups in order that the polymer has an overall cationic charge. Anionic copolymerisable monomers may be used, for instance in which the anionic group is derived from carboxylic, sulphonic or phosphonic acid.

It has been found that the cationic/zwitterionic polymer is very stable and resistant to fouling during use.

The following examples illustrate the invention.

Performance Tests

Heparin Activity

Loading of samples with heparin

1. Filter Strips.

Samples were incubated with 5 ml of a solution of heparin in PBS (usually 50 U/ml. In other experiments, a heparin concentration of 4 or 200 U/ml in saline produced the same heparin surface activity on the cationic coated surfaces) for 30 min on a test tube shaker at room temperature. After 30 min, the samples were rinsed for 10 sec on both sides first with PBS then with deionized water. The samples were dried on tissue paper and in air and stored at room temperature.

2. Whole Filters.

Arterial filters were filled with 100 ml of a heparin solution in PBS (50 U/ml) and inlet/outlet sides were closed. The filter was rotated for 30 min, ensuring that all parts of the device were in contact with the heparin loading solution. The filter was then drained and filled/drained 3 times with PBS and then filled/drained 3 times with deionized water. The filter was dried by a stream of air and stored at room temperature.

Preparation of Samples for Heparin Test

Heparin loaded filter strips (dip-coated or removed from whole arterial filters) were usually incubated for 5 hrs at 37° C. in PBS/BSA 1%/$NaN_3$ 0.1% to remove unstable bound heparin. The samples were then rinsed with PBS and deionized water as described and dried in air. Samples of 0.2–0.4× 0.4 cm were cut out and tested as described below.

Heparin Test

A chromogenic assay (Heparin CRS106, Sigma). The "Semi-Micro Method" described in the manual was used. Heparin loaded coated samples were placed in polystyrene test tubes. The tubes were placed into a 37° C. water bath (5 tubes). 200 µl of bovine factor Xa was added and the tubes were shaken. Following 1 min agitation, 200 µl factor Xa substrate was added to the tubes and they were agitated for 5 min. 200 µl acetic acid (>90%) was added to the tubes and the tubes were shaken. 200 µl of the solution was removed from the tubes and added to the well of a microplate (2 wells/sample) and measured at 405 nm against wells containing 200 µl of PBS. Previous results had shown that PBS gave the same absorbance reading as a reagent blank. The heparin activity was calculated with the use of a standard curve prepared with soluble heparin.

Platelet Adhesion

Heparin loaded and heparin free samples were incubated with human blood (citrate or heparin as anticoagulant) for 2–3 hrs and the degree of platelet adhesion was determined by scanning electron microscopy.

Fibrinogen Adsorbance

Samples of heparin loaded or heparin-free coated material were incubated with human plasma for 10 min, washed with PBS/BSA 1%, then incubated for 30 min with an anti-human fibrinogen antibody conjugated to horse radish peroxidase (Dako Code No. A080). The samples were washed and bound antibody was determined by incubating the samples with a substrate for peroxidase (O-phenylenediamine dihydrochloride, 0.4 mg/ml) and a phosphate citrate buffer with urea hydrogen peroxide (sigma P-9305). After 10 min the absorbance at 450 nm was measured against a reagent blank.

Perfusion with Bovine Blood

Two arterial filters (a control filter and a coated heparin loaded filter or a coated non-heparin loaded filter) were perfused in parallel for 6 hrs with bovine blood (3.5 L/min) at reduced heparin concentrations and macroscopic blood clots were detected visually and photographs were taken.

Observed Chloride

The counter ion in the polymeric system is chloride ion. Quantification of the chloride ion allows the level of cationic methacrylate to be determined.

Procedure

Add 0.25 g polymer to 25 ml methanol. Once the material has fully dissolved add 75 ml of distilled water to the polymer/methanol mixture. Adjust the pH of the mixture to fall between 8–9. Add 1.0 ml of potassium chromate (5% in w/v distilled water) by pipette to the flask, and titrated to the first brown/red end-point with standardised 0.01 m silver nitrate solution. Repeat the titration, using 75 ml distilled water, but no polymer sample to obtain a blank reading. The level of cationic methacrylate in the polymer is directly proportional to the chloride ion concentration.

EXAMPLE 1

Preparation of poly (2(methacryloyloxyethyl)-2'trimethylammonium) ethyl Phosphate innersalt-co-n-dodecyl methacrylate-co-11 methacryloylundecyl-1-trimethyl ammonium bromide) (40:71:8)

2-(Methacryloyloxyethyl)-2'-(trimethyl ammonium) ethyl phosphate inner salt (2.32 g, 0.0079 mole), n-dodecyl methacrylate (3.61 g, 0.0142 mole) and 11 methacryloylundecyl-1-trimethyl ammonium bromide (0.59 g, 0.0016 mole synthesised according to reference example 1) were dissolved in 43 ml of propan-2-ol and 17 ml of ethyl acetate.

This monomer solution was thoroughly degassed by bubbling dry nitrogen gas (dried over molecular sieve) through it for 30 minutes. The initiator, AIBN (0.01360 g, 0.02 weight % of solution) was then washed into the solution using 3 ml of degassed ethanol. The solution was further degassed for five minutes. Maintaining the solution under a slight positive pressure of nitrogen (equivalent to a few ml of mineral oil in a bubbler) the solution was heated to 62° C. and stirred vigorously for around 46 hours.

After this time the reaction mixture was allowed to cool to around 40° C. before removing all of the solvent using a rotary evaporator under vacuum and at about 400° C. giving a solid foam.

This foam was then dissolved in 24 ml of dichloromethane and precipitated dropwise into an excess, 200 ml, of acetone. The product was collected on a Buchner filter funnel and washed with 3 further 20 ml quantities of acetone. The white solid was dried in a vacuum oven for 16 hours at 40° C. and weighed.

The resulting polymer, obtained in 83% yield, was a white solid.

$^1$HNMR (400 MHz, d, ppm, $CD_3OD/CDCl_3$) 4.31(b), 4.21(b), 4.07(b), 3.98(b), 3.72(b),3.37, 3.33, 3.29(s), 3.22, 3.17, 1.95, 1.84(b), 1.67(b), 1.33(s), 1.06(b), 0.93(s), $C_{13}$ NMR (500 MHz, d, ppm, $CD_3OD/CDCl_3$) 176.37, 66.91, 65.90, 63.68, 60.05, 54.50, 53.37, 45.54, 32.69, 30.44, 30.13, 28.92, 26.93, 23.41, 17.31, 14.56.

EXAMPLE 2

Preparation of Poly (2(methacryloyloxyethyl)-2' trimethylammonium) ethyl phosphate innersalt-co-n-dodecyl methacrylate-co-cholinemethacrylate Using a similar technique to that used in Example 1, but using choline methacrylate (2-methacryloyloxyethyl trimethylammonium chloride) in place of 11-methacryloyl undecyl-1-trimethyl ammonium bromide, various polymerisations were carried out. The zwitterionic monomer, lauryl (dodecyl) methacrylate monomer and choline methacrylate were mixed at the molar ratio shown in Table 1 below and AIBN as initiator was used at the level shown in the table. The total weight percent of solids in the polymerisation solution is also reported in the table, since it was varied between examples.

The polymers were recovered by essentially the same method as in claim 1 although including an extra dissolution and precipitation step to remove lower molecular weight polymer.

The polymer product was subjected to chloride ion determination to establish the rate of inclusion of cationic monomer into the product. Also some rough Molecular weight determinations were carried out.

EXAMPLE 3

Preparation of Poly(2-(Methacryloyloxyethyl)-2'-(Trimethylammoniumethyl) Phosphate, Inner Salt)-co-(n-Dodecyl methacrylate)-co-(2-(Methacryloyloxy) ethyl trimethyl ammonium chloride)-co-(3-Trimethyoxysilylpropyl methacrylate) 30:60:6:4 polymers 3.1 Monomer Feed Synthesis Zwitterionic monomer (40.68 g, 0.138 mole) and cationic monomer (5.73 g, 0.0275 mole) were weighed in a glove box environment dried by $P_2O_5$. Dodecyl methacrylate (69.45 g, 0.273 mole), trimethoxysilyl monomer (4.53 g, 0.0182 mole) and α-azo-isobutyronitrile (AIBN) initiator (1.202 g, 1%) were weighed in air. A 3 neck reaction flask, fitted with water condenser, nitrogen gas flow and monomer feed tubing, and primed with anhydrous n-propanol (60 g) solvent, was immersed in a heated 90° C. oil bath. The monomers and initiator were dissolved in 300 g of n-propanol solvent and magnetically stirred in a measuring cylinder sealed with parafilm. The reaction mixture was drawn into polypropylene tubing placed inside the measuring cylinder and through silicone tubing via a peristaltic pump to enter the heated reaction vessel in a dropwise process. A complete transfer to the heated vessel took 2.25 hours. The reaction was stirred for another hour. A second charge of AIBN initiator (0.12 g), dissolved in 3 ml n-propanol, was added and the reaction mixture was stirred for a further 50 min, taking the total reaction time to 4 hours.

Once cooled to room temperature, the reaction mixture was filtered through a sintered glass filter. The solvent was removed at 40° C.–50° C. by rotary evaporator to give a white foam residue that was later redissolved in 480 ml dichloromethane and 40 ml methanol solvent mixture and dropwise precipitated into 4000 ml acetone. A white solid product settled from the acetone leaving a slightly cloudy supernatant. The product was separated by Buchner flask and 113 Whatman wet strenghtened filter paper, and dried in a room temperature vacuum oven for up to 24 hours prior to a second workup and precipitation in acetone. The product was weighed (82.9 g) to provide a 68.9 wt % yield, bottled in a brown glass vial and refrigerated.

Characterisation of Product

The polymer requires by weight C 63.08%, H 10.13%, P 3.55%, N 1.93%, Si 0.43% Cl 0.81%, found C 58.1%, H 9.98%, P 3.09%, N 1.90%, Si 0.20%, [1]Hnmr (400 MHz, ppm, $CD_3OD:CDCl_3$ 1:1 v:v) 4.34, 4.30, 3.98, 3.72, 3.38, 3.29, 3.22, 1.67, 1.32, 0.92, 0.10. Specific viscosity of 10 mg/ml solution in ethanol:chloroform (1:1 v:v) is 0.13. The polymer product, was subjected to the chloride ion assay to establish the rate of inclusion of cationic monomer; required 4.76 wt %, found 4.82 wt % and 4.94 wt %.

3.2 One Pot Synthesis

Zwitterionic monomer (4.87 g, $1.65 \times 10^{-2}$ mole), dodecyl methacrylate (8.11 g, $3.19 \times 10^{-2}$ mole), cationic monomer (0.67 g, $0.32 \times 10^{-2}$ mole) and trimethoxysilyl monomer (0.53 g, $0.21 \times 10^{-2}$ mole) were rinsed into the reaction vessel with 114 ml solvent mixture of 15:85 v/v % MeOH:EtOH. Anhydrous cationic monomer was predissolved in 3 ml pure MeOH before being rinsed into the reaction vessel. Dodecyl methacrylate monomer was pre-columned through activated basic alumina (Brockmann 1 ca.150 mesh, 50 g) before use. Dry nitrogen gas was bubbled through for 20 minutes to degas the reaction mixture at room temperature before immersing the reaction vessel in an oil bath heated to 67° C. The vessel was heated for 15 minutes prior to AIBN initiator (0.14 g) being rinsed into the reaction mixture with 2 ml solvent mixture. The reaction was magnetically stirred and maintained up a positive pressure nitrogen blanket sufficient to bubble through a mineral oil bubbler. The reaction time was 39 hours.

Once cooled to room temperature, the reaction mixture appeared clear with a slight haze. The solvent was removed at room temperature by rotary evaporator to give a white foam residue that was later redissolved in 50 ml dichloromethane and added dropwise into vigorously stirred 500 ml acetone. A white solid product settled from the acetone leaving a slightly cloudy supernatant. The product was separated by Buchner flask and 113 Whatman wet strengthened filter paper, and dried in a room temperature vacuum oven for up to 72 hours. The product was weighed to provide a 91 wt % yield, bottled in a glass jar and refrigerated.

Characterisation

The polymer requires by weight C 62.93%, H 10.11%, P 3.61%, N 1.95%, Si 0.42% Cl 0.80%, found C 57.88%, H 10.20%, P 3.30%, N 1.84%, Si 0.12% Cl 0.78%; $^1$Hnmr (400 MHz, ppm, $CD_3OD:CDCl_3$ 1:1 v:v) 4.33, 4.29, 3.97, 3.71, 3.38, 3.34, 3.29, 3.22, 1.67, 1.32, 0.92, 0.09; specific viscosity in a 10 mg/ml solution of ethanol:chloroform (1:1) is 0.32.

EXAMPLE 4

Preparation of Poly(2-Methacryloyloxyethyl)-21'-(Trimethylammoniumethyl) Phosphate. Inner Salt)-co-n-Dodecyl methacrylate)-co-(2-Methacryloyoxy) ethyl trimethyl ammonium chloride)-co-(hydroxy propyl methacrylate)-co-(3-Trimethoxysilylpropyl methacrylate) 23:47:6:20:4 polymers 4.1 Monomer Feed Synthesis Zwitterionic monomer (34.10 g, 0.116 mole) and cationic monomer (6.3 g, 0.030 mole) were weighed in a glove box environment dried by $P_2O_5$. Dodecyl methacrylate (60.01, g 0.236 mole), hydroxypropyl methacrylate monomer (14.51 g, 0.101 mole), trimethyoxysilyl monomer (5.00 g, 0.020 mole) and AIBN initiator (0.2409 g, 0.2%) were weighed in air. A 3 neck reaction flask, fitted with water condenser, nitrogen gas flow and monomer feed tubing, and primed with anhydrous n-propanol:isopropyl acetate (60:40 mass ratio) solvent, was immersed in a heated 90° C. oil bath. The monomers and initiator were dissolved in n-propanol:isopropyl acetate solvent and magnetically stirred in a measuring cylinder_sealed with parafilm. The reaction mixture was drawn into polypropylene tubing placed inside the measuring cylinder and through silicone tubing via a peristaltic pump to enter the heated reaction vessel in a dropwise process. A complete transfer to the heated vessel took 2 hours. The reaction was stirred for another hour. A second charge of AIBN initiator (0.0241 g, 0.02 wt %) was added and the reaction mixture was stirred for a further hour, taking the total reaction time to 4 hours. Total solids content was 30 wt % in n-propanol:isopropyl acetate (168.06 g:112.08 g).

Once cooled to room temperature, the reaction mixture was split into two batches. The first batch of reaction mixture (240 ml) was precipitated by dropwise addition to vigorously stirred methyl acetate (2000 ml). The product was separated by Buchner flask and 113 Whatman wet strengthened filter paper, and dried in a room temperature vacuum oven for up to 24 hours. The product was rapidly frozen by liquid nitrogen, milled into a fine powder and further dried in a room temperature vacuum for 24 hours. The product (50.67 g, 81.8% based on mass recovery) was bottled in a brown glass vial and stored at 4° C.

The polymer requires by weight C 62.4%, H 9.9%, P 3.0%, N 1.9%, Si 0.4% Cl 0.8%, found: C 57.0%, H 9.4%, N 1.7%, P 2.7%; $^1$Hnmr (400 MHz, ppm, $CD_3OD:CDCl_3$ 1:1 v:v) 4.41, 4.08, 3.83, 3.46, 3.40, 3.34, 2.07, 1.67, 1.43, 1.18, 1.04.

The product was subjected to chloride ion assay to establish the rate of inclusion of cationic monomer: required 5.23 wt %, found 4.66 and 4.71 wt %.

4.2 One Pot Synthesis

Zwitterionic monomer (3.98 g, $1.35 \times 10^{-2}$ mole), dodecyl methacrylate monomer (7.009 g, $2.76 \times 10^{-2}$ mole), cationic monomer (0.733 g, $0.35 \times 10^{-2}$ mole), hydroxypropyl methacrylate monomer (1.691 g, $0.67 \times 10^{-2}$ mole) and trimethoxysilyl monomer (0.585 g, $0.24 \times 10^{-2}$ mole) were rinsed into the reaction vessel with 98 ml solvent mixture of 15:85 v:v % MeOH:EtOH. Anhydrous cationic monomer was predissolved in 3 ml pure MeOH before being rinsed into the reaction vessel. Dodecyl methacrylate was pre-columned through activated basic alumina (Brockmann 1 ca.150 mesh, 50 g) before use. Dry nitrogen gas was bubbled through for 20 minutes to degas the reaction mixture at room temperature before immersing the reaction vessel in an oil bath heated to 67° C. The vessel was heated for 15 minutes prior to AIBN initiator (0.14 g, 1.1 wt %) being rinsed into the reaction mixture with 2 ml solvent mixture. The reaction was magnetically stirred and maintained under a positive pressure nitrogen blanket sufficient to bubble through a mineral oil bubbler. The reaction time was 39.5 hours.

Once cooled to room temperature, the reaction mixture was filtered through sintered glass. The solvent was removed at <40° C. by rotary evaporator to give a white foam residue that was later redissolved in 58 ml dichloromethane and added dropwise into vigorously stirred 600 ml acetone. A white solid product settled from the acetone leaving a slightly cloudy supernatant. The product was separated by Buchner flask and 113 Whatman wet strengthened filter paper, and dried in a room temperature vacuum oven for up to 20 hours. The product was milled, further dried in a room temperature vacuum for 24 hours and weighed to provide a 93.2 wt % yield, bottled in a glass jar and refrigerated.

The polymer requires by weight C 62.41%, H 9.91%, P 2.99%, N 1.70%, Si 0.47%, Cl 0.89%, found C 58.45%, H 9.45%, P 2.55%, N 1.65% Si 0.34%, Cl 1.06%. $^1$Hnmr (400 MHz, ppm, $CD_3OD:CDl_3$ 1:1 v:v) 4.33, 4.29, 3.97, 3.71, 3.38, 3.34, 3.29, 3.22, 1.67, 1.32, 0.92, 0.09. Specific viscosity of 10 mg/ml solution in ethanol is 0.33. The polymer product was subjected to the chloride ion assay to establish the rate of inclusion of cationic monomer; required 5.24 wt %, found 5.16 wt % and 5.26 wt %.

EXAMPLE 5

Preparation of Poly(2Methacryloyloxyethyl) 2' (Trimethylammoniumethyl) Phosphate. Inner Salt)-co-(n Dodecyl methacrylate)-co-(2Methacryloyloxy) ethyl trimethyl ammonium chloride) 33.3:60:6.7 polymers Monomer Feed Synthesis To anhydrous n-propanol:isopropyl acetate (30.0 g:8.0 g) solvent mixture at room temperature, zwitterionic monomer (13.5 g, $4.58 \times 10^{-2}$ mole) dodecyl methacrylate (20.9 g, $8.23 \times 10^{-2}$ mole) and cationic monomer (2.5 g, $1.20 \times 10^{-2}$ mole) were added. To the mixture, AIBN (0.7 g, 0.20 wt %), dissolved 4 g isopropyl acetate, was added. The stirred mixture was parafilm sealed in a measuring cylinder and dropwise added via a peristaltic pump to stirred anhydrous n-propanol: isopropyl acetate (27 g:20 g) solvent mixture immersed in a heated 90° C. oil bath under $N_2$ gas flow. Complete transfer took 2 hours. The pump tubing was washed with isopropyl acetate (4 g) and n-propanol 4 g) into the 90° C. reaction mixture. The reaction was stirred for another hour, where upon AIBN, (0.01 g, 0.02 wt %) dissolved 2 ml isopropyl acetate, was added, the pump tubing was washed with isopropyl acetate (2 g) and the reaction was stirred for a further hour.

The heating was stopped after 4 hours and the reaction mixture was pumped to ethyl acetate (450 g) at room temperature followed by a pump line wash of n-propanol (3 g). The product was allowed to settle and the supernatant was decanted. Product was dissolved with isopropanol (47 g) solvent, pumped to ethyl acetate (720 g) for 45 minutes, the pump line washed with isopropanol (6 g) and the product allowed to settle. The supernatant was decanted and the product was washed with acetone (160 g) by stirring for 10 minutes. The supernatant was decanted and the product was filtered (Whatman 13 wet strengthened paper) with an acetone wash (80 g). The product was dried at room temperature in a vacuum deccicator for up to 16 h, weighed (31.6 g, 87% yield based on mass recovery) and stored in a brown glass vial at 4° C.

Characterisation $^1$Hnmr (400 MHz, ppm, $CD_3OD:CDCl_3$ 1:1 v:v) 4.41, 4.08, 3.83, 3.46, 3.40, 3.34, 2.07, 1.67, 1.43, 1.18; Specific viscosity of 10 mg/ml solution in ethanol is 0.26.

The polymer was subjected to chloride ion assay to establish inclusion of cationic monomer, required 5.23 wt %, found 5.28 and 5.36 wt %.

EXAMPLE 6

Samples of some of the polymers of examples 1 and 2 were tested for their performance in terms of fibrinogen adsorption and heparin activity. A coating solution of the polymer 10 mg/ml in isopropyl alcohol, was made up and used to coat the surface of samples of polyethylene terephthalate (p.e.t.). The p.e.t. sample to be subjected to a fibrinogen assay was a 1×3 cm sheet, whilst that to be subjected to a heparin assay was 40 micron woven filter material. The dried coating was subsequently contacted with heparin solution 50 U/ml in PBS, rinsed first with PBS and then with deionised water and dried. The polymer/heparin coated substrate was subjected to the fibrinogen and heparin tests mentioned above. The results for the heparin activity and fibrinogen adsorption for the polymers of example 2 are given in Table 2 below.

Furthermore example 1 polymer/heparin coated materials were subjected to a stability test. For this the polymer (example 1)/heparin coated substrates were immersed in 1% serum albumin in phosphate buffered saline for periods in the range 0.5 to 6 hours at 37° C. The treated samples were removed, rinsed first with PBS and then with deionised water, and the heparin activity measured. The results indicate that there is no significant loss of activity after 6 hours of BSA/PBS incubation, whereas comparative tests carried out on the commercially available Duraflo and Medtronic M-40 surfaces showed very poor stability. The results using the Carmeda Bioactive surface showed equivalent stability.

EXAMPLE 7

As a further performance test, substrates coated with example 1 polymer, with and without heparin loading, were contacted with heparinised blood 15 U/ml for 60 minutes. The treated samples were removed, rinsed first with PBS and then with deionised water and the heparin activity measured. The results show that surfaces coated with the polymer with pendant cationic and phosphoryl choline groups attract and bind heparin from blood which contains heparin. The surfaces were also studied under s.e.m. and no biological deposits (e.g. of platelets, blood cells and protein) were observed, for the heparin loaded sample or the non-heparin loaded sample.

As comparisons, tests were also carried out on three commercially available heparinised surfaces. DuraFlo uses ionically bound heparin; Medtronic M-40 is believed to use ionically bound heparin; Medtronic CBM-40 (Carmeda Bioactive) uses end point attached heparin.

For these experiments, filter samples were incubated at room temperature with 5 ml of phosphate buffered saline (PBS) with or without 1% serum albumin (BSA) or fresh heparinized human blood. After 60 min, the samples were rinsed thoroughly with saline and deionised water and heparin activity was measured.

The results are shown in Table 3.

Before incubation with PBS, the heparin activity on the DurafloII sample was 240 mU/cm$^2$ and 33.5 mU/cm$^2$ on the Medtronic M40. The Carmeda BioActive Surface heparin appeared to be more stable with BSA, but the initial heparin activity was the lowest of all filters tested. Previous results have shown that another 20 micron Medtronic filter with Carmeda bonded heparin had only 2,3 mU/cm$^2$.

Table 3 shows that the polymer of the invention attracts and binds heparin from the blood sample which had a heparin concentration of 15 U/ml.

Initial results had shown that the coating not loaded with heparin shows heparin activity following incubation with heparin containing human blood (see Table 3).

Two similar arterial filters were coated with the cationic/zwitterionic heparin binding polymer of example 1. only one filter was loaded with heparin as described above, the other filter was only washed with PBS. Both filters were perfused in parallel with bovine blood (3.5 L/min) for 6 hrs. The blood contained 644 U heparin/kg. The activated clotting time (measured by the Hemochron method) of the system was 447 sec after 9 min perfusion and fell to 257 sec after 60 min perfusion. After 306 min perfusion, the activated clotting time was 212 sec. Both filters performed similar and showed significantly less blood clots than uncoated filters in similar previous perfusion experiments.

EXAMPLE 8

Further samples of polymers of examples 1 and 3 to 5 were coated onto arterial filters using the coating solutions described in example 6. The filters were dip coated with the polymer solutions, which were then dried overnight. The polymers of examples 3 and 4 were kept at 70° C. overnight to ensure complete crosslinking. The filters were then tested for their fibrinogen adsorption using the performance test described above. Some samples of filter were, after coating with polymer, were loaded with heparin using the general test described above and then subjected to fibrinogen adsorption and heparin activity tests. The control was untreated filter. Table 4 shows the results for reduction in fibrinogen adsorption as compared to the control and heparin activity for the heparin loaded devices. Comparisons are quoted for two commercially available heparin coatings Medtronic CB-M40, believed to have covalently (end point attached) heparin and Medtronic M-40 believed to have ionically bound heparin, in terms of fibrinogen adsorption and heparin activity. The results show that heparin is adsorbed onto the polymer, the mechanism assumed to be an ion exchange process. The filters coated with the PC polymer have reduced fouling by fibrinogen.

TABLE 1

| Example | AIBN wt % | Total Solids % | Pm g | Pm Mol % | MI g | MI Mol % | Cm g | Cm Mol % | Temp C. | Yield % | Cl—Calc (mg/l) | Cl—Obs (mg/l) | MW |
|---|---|---|---|---|---|---|---|---|---|---|---|---|---|
| 2.1 | 2.0 | 14.7 | 5.4 | 36.6 | 8.4 | 57.0 | 0.9 | 6.4 | 61 | 75.6 | 83.6 | 76.6 | 900780 |
| 2.2 | 1.0 | 14.7 | 5.4 | 36.9 | 8.3 | 56.8 | 0.9 | 6.4 | 61 | 74.3 | 83.0 | 80.4 | 678664 |
| 2.3 | 0.2 | 14.7 | 5.4 | 36.6 | 8.4 | 56.9 | 1.0 | 6.5 | 61 | 70.5 | 84.7 | 74.7 | 1597718 |
| 2.4 | 0.1 | 14.7 | 5.4 | 36.7 | 8.3 | 56.8 | 1.0 | 6.5 | 61 | 70.7 | 84.8 | 81.4 | 1850975 |
| 2.5 | 0.2 | 12.2 | 5.5 | 37.4 | 8.7 | 59.2 | 0.5 | 3.4 | 61 | 57.7 | 44.4 | 68.0 | 616454 |
| 2.6 | 0.2 | 12.2 | 5.4 | 37.2 | 8.7 | 59.4 | 0.5 | 3.4 | 61 | 72.6 | 44.6 | 37.1 | |
| 2.7 | 0.2 | 12.3 | 5,4 | 37.0 | 8.3 | 56.8 | 0.9 | 6.2 | 61 | 48.3 | 81.0 | 84.0 | |
| 2.8 | 0.2 | 14.7 | 5.4 | 36.7 | 8.4 | 56.9 | 0.9 | 6.4 | 61 | 49.9 | 83.6 | 71.7 | 493906 |
| 2.9 | 0.2 | 14.7 | 5.4 | 36.7 | 8.4 | 56.9 | 0.9 | 6.4 | 61 | 67.3 | 83.6 | 73.4 | |
| 2.10 | 0.2 | 12.2 | 5.4 | 36.8 | 8.4 | 57.1 | 0.9 | 6.1 | 61 | 73.6 | 79.8 | 70.4 | 395537 |
| 2.11 | 0.2 | 13.4 | 5.4 | 36.6 | 8.4 | 57.0 | 0.9 | 6.4 | 61 | 77.8 | 83.4 | 74.3 | |
| 2.12 | 0.2 | 13.4 | 5.4 | 36.6 | 8.4 | 57.0 | 0.9 | 6.4 | 61 | 82.6 | 83.4 | 77.6 | 668891 |
| 2.13 | 0.2 | 12.4 | 5.5 | 37.0 | 6.9 | 46.3 | 2.5 | 16.7 | 61 | 75.4 | 224.4 | 226.0 | 346592 |
| 2.14 | 0.2 | 14.8 | 5.4 | 36.8 | 6.9 | 46.4 | 2.5 | 16.8 | 61 | 78.9 | 226.1 | 187.3 | |
| 2.15 | 0.2 | 12.5 | 5.5 | 36.3 | 4.6 | 30.4 | 5.0 | 33.3 | 61 | 68.7 | 467.9 | 524.0 | 685687 |

*The molecular weights are relative values of determinations by gel permeation chromatograhpy (without calibration) but should approximate to Daltons

TABLE 2

| Example | Heparin Activity mU/cm2 | Fibrinogen reduction % |
|---|---|---|
| 2.5 | 15.9 | 79 |
| 2.6 | 11.8 | 55 |
| 2.7 | 24.3 | 66 |
| 2.8 | 21.2 | 74 |
| 2.9 | 36.2 | 60 |
| 2.10 | 22.1 | 64 |
| 2.11 | 18.7 | 67 |
| 2.12 | 35.6 | 70 |
| 2.13 | 0.9 | 81 |
| 2.14 | 1.8 | 57 |
| 2.15 | 0 | 77 |

TABLE 3

Heparin activity in mU/cm2 fallawing incubatian with

| Sample | PBS | PBS/BSA | BLOOD heparinised |
|---|---|---|---|
| DurafloII | 25.6 | 4.8 | 0 |
| Medtronic M-40 | 7.1 | 0.9 | 0 |
| Medtronic CBM-40 | 5 | 4 | — |
| Ex.1/ Heparin | 33.1 | 18.1 | 16.4 |
| EX 1 | — | 0 | 18.3 |

TABLE 4

| Polymer of Example | Without Heparin Loading % reduction fibrinogen | With Heparin Loading % reduction fibrinogen | With Heparin Loading Heparin activity MU/cm² |
|---|---|---|---|
| Control | 0 | 100 | |
| 1 | 92 | 87 | 42 |
| 3 | 90 | 82 | 14 |
| 4 | 91 | 88 | 13 |
| 5 | 91 | 89 | 39 |
| comparison covalently bound Heparin | N/A | 56 | 9 |
| comparison ionically bound Heparin | N/A | 7 | <1 |

REFERENCE EXAMPLE 1

Synthesis of 11-methacryloyl undecyl-1-trimethylammonium bromide.

Step 1

To a solution of 11-bromo-1-undecanol (5.05 g, 0.02 mol), triethylamine (2.86 g, 0.028 mol) in dry ethyl acetate (30 ml), a solution of methacroyl chloride (3.03 g, 0.029 mol) in ethyl acetate (20 ml) was slowly added, and the resulting mixture stirred for 90 min at RT.

The solid was filtered off, and the solvents removed in vacuo to afford predominantly 1-bromo, 11-undecylmethacrylate (Yield 6.26 g, 97%). As no starting materials were observed by 1H NMR and TLC Rf 0.69 (chloroform/pet. ether 7:3, v/v), this material was carried through to the second step.

Step 2

The product of step 1 (6.26 g, 0.019 mol) was dissolved in dry acetonitrile (40 ml) and added to a mixture of trimethylamine (2.8 g, 0.047 mol) in acetonitrile (20 ml). The system was purged with nitrogen, and then sealed with a dry ice condenser. The reaction was heated to 50 degrees for 20 hr, and protected from light with aluminium foil.

The remaining trimethylamine was removed on a water pump, and then the solvents removed in vacuo to give an off-white powder. This was washed with ether (250 ml) and the white solid collected (5.67 g, 76% yield). The ether was evaporated to dryness, and the residue again treated with ether (100 ml) to yield further white solid (1.02 g, 13%). 1H NMR indicated that the desired product was formed.

What is claimed is:

1. An ion-exchange process in which an aqueous solution which contains dissolved or suspended anionic compound is contacted with anion exchange material having pendant cationic groups and anionic counterions whereby the anionic compound is ion exchanged with the counterion characterised in that the anion exchange material also has pendant zwitterionic groups, which comprise a cationic moiety and an anionic moiety, and in that the pendant cationic group $Q^1$ is a group $N^+R^5_3$, $P^+R^5_3$ or $S^+R^5_2$ in which the groups $R^5$ are the same or different and are each $C_{1-4}$-alkyl or aryl or two of the groups $R^5$ together with the heteroatom to which they are attached form a saturated or unsaturated heterocyclic ring containing from 5 to 7 atoms.

2. A process according to claim 1 in which in the pendant zwitterionic group, the cationic moiety is a quaternary ammonium group.

3. A process according to claim 1 in which in the pendant zwitterionic group, the anionic moiety is a phosphate or a phosphonate group.

4. A process according to claim 3, in which the anionic moiety is a phosphate diester group.

5. A process according to claim 1 in which $Q^1$ is $N^+R^5_3$ in which each $R^5$ is $C_{1-4}$alkyl.

6. A process according to claim 5, wherein $R^5$ is methyl.

7. A process according to claim 1 in which the anion exchange material comprises a substrate coated with a polymer having pendant zwitterionic groups and pendant cationic groups.

8. A process according to claim 7 in which the polymer is formed from monomers including a) a zwitterionic monomer of the formula I

YBX    I wherein B is a bond or a straight or branched alkylene, alkylene-oxa-alkylene, or alkylene oligooxa alkylene group any of which optionally includes one or more fluorine substituents;

X is an organic group having a zwitterionic moiety; and

Y is an ethylenically unsaturated polymerisable group; and b) a cationic monomer of the formula II

Y¹B¹Q¹    II wherein $B^1$ is a bond or a straight or branched alkylene, alkylene-oxa-alkylene or alkylene-oligooxa-alkylene group, any of which optionally includes one or more fluorine substitutents;

$Y^1$ is an ethylenically unsaturated polymerisable group; and $Q^1$ is a group $N^+R^5_3$, $P^+R^5_3$ or $S^+R^5_2$ in which the groups $R^5$ are the same or different and are each $C_{1-4}$-alkyl or aryl or two of the groups $R^5$ together with the heteroatom to which they are attached form a saturated or unsaturated heterocyclic ring containing from 5 to 7 atoms.

9. A process according to claim 8 in which the monomers further comprise a hydrophobic monomer of the formula III

Y²B²Q²    III wherein $B^2$ is a bond or a straight or branched alkylene, alkylene-oxa-alkylene or alkylene-oligooxa-alkylene group, any of which may optionally include one or more fluorine substituents;

$Y^2$ is an ethylenically unsaturated polymerisable group; and $Q^2$ is an organic group having a hydrophobic group selected from alkyl groups having at least six carbon atoms, fluorine substituted alkyl groups and alkyl groups having at least one siloxane substituent.

10. A process according to claim 9 in which $B^2$ and $Q^2$ together represent a $C_{6-24}$-alkyl group optionally including carbon-carbon unsaturated bonds.

11. A process according to claim 10, in which $B^2$ and $Q^2$ together represent a straight chain $C_{8-16}$-alkyl group.

12. A process according to claim 9, in which $Y^2$ is selected from

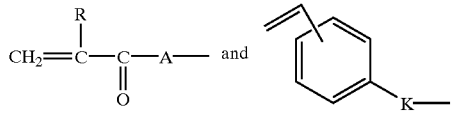

wherein:

R is hydrogen or a $C_{1-4}$-alkyl group;

A is —O— or —NR¹—, where $R^1$ is hydrogen or a $C_{1-4}$-alkyl group or $R^1$ is —B²Q²; and K is selected from the group consisting of —(CH₂)$_p$OC(O)—, —(CH₂)$_p$C(O)O—, —(CH₂)$_p$OC(O)O—, —(CH₂)$_p$NR²—, —(CH₂)$_p$NR²C(O)—, —(CH₂)$_p$C(O)NR²—, —(CH₂)$_p$NR²C(O)O—, —(CH₂)$_p$OC(O)NR²—, —(CH₂)$_p$NR²C(O)NR²—, —(CH₂)$_p$O—, —(CH₂)$_p$SO₃—, and a valence bond, wherein p is from 1 to 12 and $R^2$ is hydrogen or a $C_1$–$C_4$ alkyl group, and wherein in the formula —(CH₂)$_p$NR²C(O)NR²— the $R^2$ groups may be the same or different.

13. A process according to claim 8 in which the monomers additionally include a crosslinkable comonomer of the formula IV

Y³B³Q³    IV wherein $B^3$ is a bond or a straight or branched alkylene, alkylene-oxa-alkylene or alkylene-oligooxa-alkylene group, any of which optionally includes one or more fluorine substituents;

$Y^3$ is an ethylenically unsaturated polymerisable group; and $Q^3$ is an organic group having a reactive group capable, on imposition of an external stimulus, of reacting with a coreactive group which is pendant on the polymer.

14. A process according to claim 13 which $Y^3$ is selected from

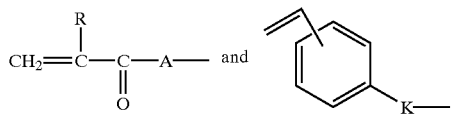

wherein:

R is hydrogen or a $C_{1-4}$-alkyl group;

A is —O— or —NR¹—, where $R^1$ is hydrogen or a $C_{1-4}$-alkyl group or $R^1$ is —B³Q³, where $B^3$ and $Q^3$ are the same as defined with respect to the formula IV, K is selected from the group consisting of —(CH$_2$)$_p$OC(O)—, —(CH$_2$)$_p$C(O)O—, —(CH$_2$)$_p$OC(O)O—, —(CH$_2$)$_p$NR$^2$—, —(CH$_2$)$_p$NR$^2$C(O)—, —(CH$_2$)$_p$C(O)NR$^2$—, —(CH$_2$)$_p$NR$^2$C(O)O—, —(CH$_2$)$_p$OC(O)NR$^2$—, —(CH$_2$)$_p$NR$^2$C(O)NR$^2$—, —(CH$_2$)$_p$O—, —(CH$_2$)$_p$SO$_3$—, and a valence bond, wherein p is from 1 to 12 and R$^2$ is hydrogen or a C$_1$–C$_4$ alkyl group, and wherein in the formula —(CH$_2$)$_p$NR$^2$C(O)NR$^2$— the R$^2$ groups may be the same or different.

15. A process according to claim 8 in which Y and Y$^1$ are each independently selected from

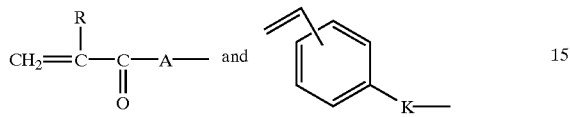

wherein:
R is hydrogen or a C$_1$–C$_4$ alkyl group;
A is —O— or —NR$^1$— where R$^1$ is hydrogen or a C$_1$–C$_4$ alkyl group or R$^1$ is —B—X or —B$^1$Q$^1$ where
B, B$^1$, Q$^1$ and X are the same as defined with respect to the formulae I and II and
K is selected from the group consisting of —(CH$_2$)$_p$OC(O)—, —(CH$_2$)$_p$C(O)O—, —(CH$_2$)$_p$OC(O)O—, —(CH$_2$)$_p$NR$^2$—, —(CH$_2$)$_p$NR$^2$C(O)—, —(CH$_2$)$_p$C(O)NR$^2$—, —(CH$_2$)$_p$NR$^2$C(O)O—, —(CH$_2$)$_p$OC(O)NR$^2$—, —(CH$_2$)$_p$NR$^2$C(O)NR$^2$—, —(CH$_2$)$_p$O—, —(CH$_2$)$_p$SO$_3$—, and a valence bond, wherein p is from 1 to 12 and R$^2$ is hydrogen or a C$_1$–C$_4$ alkyl group, and wherein in the formula —(CH$_2$)$_p$NR$^2$C(O)NR$^2$— the R$^2$ groups may be the same or different.

16. A process according to claim 15 in which the monomers further comprise a hydrophobic monomer of the formula III

Y$^2$B$^2$Q$^2$     III wherein:
B$^2$ is a bond or straight or branched alkylene, alkylene-oxa-alkylene or alkylene-oligo oxaalkylene group, any of which may optionally include one or more fluorine substituents;
Y$^2$ is an ethylenically unsaturated polymerisable group selected from

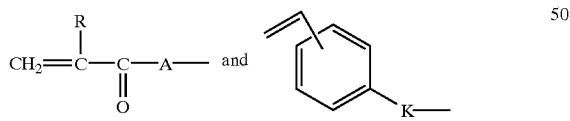

wherein:
R is hydrogen or a C$_{1-4}$-alkyl group;
A is —O— or —NR$^1$—, where R$^1$ is hydrogen or a C$_{1-4}$-alkyl group or R$^1$ is —B$^2$Q$^2$, and
K is selected from the group consisting of —(CH$_2$)$_p$OC(O)—, —(CH$_2$)$_p$C(O)O—, —(CH$_2$)$_p$OC(O)O—, —(CH$_2$)$_p$NR$^2$—, —(CH$_2$)$_p$NR$^2$C(O)—, —(CH$_2$)$_p$C(O)NR$^2$—, —(CH$_2$)$_p$NR$^2$C(O)O—, —(CH$_2$)$_p$OC(O)NR$^2$—, —(CH$_2$)$_p$NR$^2$C(O)NR$^2$—, —(CH$_2$)$_p$O—, —(CH$_2$)$_p$SO$_3$—, and a valence bond, wherein p is from 1 to 12 and R$^2$ is hydrogen or a C$_1$–C$_4$ alkyl group, and wherein in the formula —(CH$_2$)$_p$NR$^2$C(O)NR$^2$— the R$^2$ groups may be the same or different, and Q$^2$ is an organic group having a hydrophobic group selected from alkyl groups having at least six carbon atoms, fluorine substituted alkyl groups and alkyl groups having at least one siloxane substituent; and
in which the monomers additionally include a crosslinkable comonomer of the formula IV

Y$^3$B$^3$Q$^3$     IV wherein B$^3$ is a bond or a straight or branched alkylene, alkylene-oxa-alkylene or alkylene-oligo oxa alkylene group, any of which optionally includes one or more fluorine substituents;
Y$^3$ is an ethylenically unsaturated polymerisable group selected from

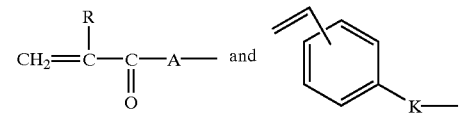

wherein:
R is hydrogen or a C$_{1-4}$-alkyl group;
A is —O— or —NR$^1$—, where R$^1$ is hydrogen or a C$_{1-4}$-alkyl group or R$^1$ is —B$^2$Q$^2$; and
K is a group —(CH$_2$)$_p$OC(O)—, —(CH$_2$)$_p$C(O)O—, —(CH$_2$)$_p$OC(O)O—, —(CH$_2$)$_p$NR$^2$—, —(CH$_2$)$_p$NR$^2$C(O)—, —(CH$_2$)$_p$C(O)NR$^2$—, —(CH$_2$)$_p$NR$^2$C(O)O—, —(CH$_2$)$_p$OC(O)NR$^2$—, —(CH$_2$)$_p$NR$^2$C(O)NR$^2$—, —(CH$_2$)$_p$O—, —(CH$_2$)$_p$SO$_3$—, and a valence bond, wherein p is from 1 to 12 and R$^2$ is hydrogen or a C$_1$–C$_4$ alkyl group, and wherein in the formula —(CH$_2$)$_p$NR$^2$C(O)NR$^2$— the R$^2$ groups may be the same or different and Q$^3$ is an organic group having a reactive group capable, on imposition of an external stimulus, of reacting with a coreactive group which is pendant on the polymer.

17. A process according to claim 16 in which each of Y, Y$^1$, Y$^2$ and Y$^3$ represents the same group.

18. A process according to claim 8 in which B and B$^1$ each represent a straight or branched C$_{1-24}$ alkylene group.

19. A process according to claim 8 in which X is an ammonium phosphate ester group, the zwitterionic monomer having the formula

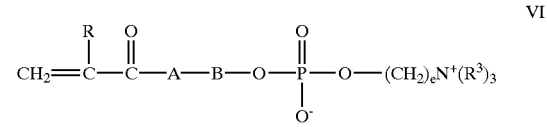

wherein R is hydrogen or a C$_1$–C$_4$ alkyl group,
A is —O— or NR$^1$, where R$^1$ is hydrogen or a C$_1$–C$_4$ alkyl group;
B is a bond or a straight or branched alkylene, alkylene-oxa-alkylene or alkylene-oligooxa-alkylene group, any of which optionally includes one or more fluorine substituents;
the groups R$^3$ are the same or different and each is hydrogen, C$_{1-24}$ alkyl, aryl, alkaryl, aralkyl, or two or three of the groups R$^3$ together with the nitrogen atom to which they are attached form a saturated or unsaturated heterocyclic ring; and e is 1 to 6.

20. A process according to claim 1 in which the solution has suspended or dissolved therein an anionically charged mucopolysaccharide.

21. An ion exchange material comprising a substrate having
pendant cationic groups each of which is a group $Q^1$ which is $N^+R^5_3$, $P^+R^5_3$ or $S^+R^5_2$,
in which the groups $R^5$ are the same or different and are each $C_{1-4}$-alkyl or aryl or two of the groups $R^5$ together with the heteroatom to which they are attached form a saturated or unsaturated heterocyclic ring containing from 5 to 7 atoms; and
pendant zwitterionic groups X, which comprise a cationic moiety and an anionic moiety, in which the cationic moiety is a quaternary ammonium or phosphonium group or a tertiary sulphonium group.

22. A material according to claim 21 in which the anionic moiety of the zwitterion X is a phosphate or a phosphonate group.

23. A material according to claim 22 in which X is a group of formula

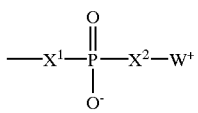

(VI)

in which the moieties $X^1$ and $X^2$, which are the same or different, are —O—, —S—, —NH— or a valence bond, and $W^+$ is a group comprising an ammonium, phosphonium or sulphonium cationic group and a group linking the anionic and cationic moieties which is $C_{1-12}$-alkylene group.

24. A material according to claim 23 in which $W^+$ contains a quaternary ammonium group.

25. A material according to claim 24 in which the substrate is polyester, polyolefin, polycarbonate, polyvinyl chloride, steel, or cellulose or silica.

26. A material according to claim 23 in which $W^+$ is a group of formula

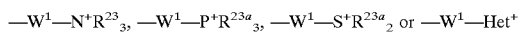

in which:
$W^1$ is alkylene of 1 or more carbon atoms optionally containing one or more ethylenically unsaturated double or triple bonds, disubstituted-aryl, alkylene aryl, aryl alkylene, or alkylene aryl alkylene, disubstituted cycloalkyl, alkylene cycloalkyl, cycloalkyl alkylene or alkylene cycloalkyl alkylene, which group $W^1$ optionally contains one or more fluorine substituents and/or one or more functional groups; and either
the groups $R^{23}$ are the same or different and each is hydrogen or alkyl of 1 to 4 carbon atoms, or aryl, or two of the groups $R^{23}$ together with the atom to which they are attached form a heterocyclic ring containing from 5 to 7 atoms or the three groups $R^{23}$ together with the atom to which they are attached form a fused ring structure containing from 5 to 7 atoms in each ring, and optionally one or more of the groups $R^{23}$ is substituted by a hydrophilic functional group, and
the groups $R^{23a}$ are the same or different and each is $R^{23}$ or a group $OR^{23}$, where $R^{23}$ is as defined above; or
Het is an aromatic nitrogen-, phosphorous- or sulphur-containing ring.

27. A material according to claim 26 in which $W^1$ is a straight-chain alkylene group.

28. A material according to claim 22 in which X is a group of formula (VA):

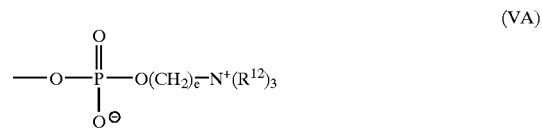

(VA)

where the groups $R^{12}$ are the same or different and each is hydrogen or $C_{1-4}$ alkyl, and e is from 1 to 6.

29. A material according to claim 22, in which the anionic moiety is a phosphate diester.

30. A material according to claim 21 which comprises a substrate coated with a polymer formed from monomers including
a) a zwitterionic monomer of the formula I

wherein B is a bond or a straight or branched alkylene, alkylene-oxa-alkylene, or alkylene oligooxa-alkylene group any of which optionally includes one or more fluorine substituents;
X is an organic group having a zwitterionic moiety; and
Y is an ethylenically unsaturated polymerisable group; and
(b) a cationic monomer of the formula II

wherein $B^1$ is a bond or a straight or branched alkylene, alkylene-oxa-alkylene or alkylene-oligooxa-alkylene group, any of which optionally includes one or more fluorine substituents;
$Y^1$ is an ethylenically unsaturated polymerisable group; and
$Q^1$ is $N^+R^5_3$, $P^+R^5_3$ or $S^+R^5_2$, in which the groups $R^5$ are the same or different and are each $C_{1-4}$-alkyl or aryl or two of the groups $R^5$ together with the heteroatom to which they are attached form a saturated or unsaturated heterocyclic ring containing from 5 to 7 atoms.

31. A material according to claim 30 in which the substrate is in the form of a membrane.

* * * * *